(12) United States Patent
Meretzki

(10) Patent No.: US 11,433,163 B2
(45) Date of Patent: Sep. 6, 2022

(54) BONE REPAIR COMPOSITIONS

(71) Applicant: BONUS THERAPEUTICS LTD., Haifa (IL)

(72) Inventor: Shai Meretzki, Haifa (IL)

(73) Assignee: BONUS THERAPEUTICS LTD., Haifa (IL)

( * ) Notice: Subject to any disclaimer, the term of this patent is extended or adjusted under 35 U.S.C. 154(b) by 0 days.

(21) Appl. No.: 15/303,011

(22) PCT Filed: Apr. 9, 2015

(86) PCT No.: PCT/IL2015/050380
§ 371 (c)(1),
(2) Date: Oct. 10, 2016

(87) PCT Pub. No.: WO2015/155777
PCT Pub. Date: Oct. 15, 2015

(65) Prior Publication Data
US 2017/0028104 A1    Feb. 2, 2017

Related U.S. Application Data

(60) Provisional application No. 61/977,691, filed on Apr. 10, 2014.

(51) Int. Cl.
| | |
|---|---|
| *A61L 27/38* | (2006.01) |
| *A61L 27/46* | (2006.01) |
| *A61L 27/36* | (2006.01) |
| *A61K 31/728* | (2006.01) |
| *A61K 35/28* | (2015.01) |
| *A61K 35/44* | (2015.01) |
| *A61L 27/12* | (2006.01) |
| *A61L 27/58* | (2006.01) |
| *A61L 27/20* | (2006.01) |

(52) U.S. Cl.
CPC ........ *A61L 27/3891* (2013.01); *A61K 31/728* (2013.01); *A61K 35/28* (2013.01); *A61K 35/44* (2013.01); *A61L 27/12* (2013.01); *A61L 27/20* (2013.01); *A61L 27/3604* (2013.01); *A61L 27/3608* (2013.01); *A61L 27/3808* (2013.01); *A61L 27/3834* (2013.01); *A61L 27/3847* (2013.01); *A61L 27/46* (2013.01); *A61L 27/58* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,186,448 A | 2/1980 | Brekke |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,133,755 A | 7/1992 | Brekke |
| 5,192,659 A | 3/1993 | Simons |
| 5,272,057 A | 12/1993 | Smulson et al. |
| 5,281,521 A | 1/1994 | Trojanowski et al. |
| 5,514,378 A | 5/1996 | Mikos |
| 5,522,895 A | 6/1996 | Mikos |
| 5,607,474 A | 3/1997 | Athanasiou |

(Continued)

FOREIGN PATENT DOCUMENTS

| | | |
|---|---|---|
| DE | 3810803 A1 | 10/1989 |
| WO | 9959500 A2 | 11/1999 |

(Continued)

OTHER PUBLICATIONS

Nassiri et al., "Interactions of Mesenchymal Stem Cells with Endothelial Cells", Stem Cells and Development, Prepublished online Oct. 30, 2013, vol. 23, No. 4, pp. 319-332.*
Duttenhoefer et al., "3D Scaffolds Co-Seeded With Human Endothelial Progenitor and Mesenchymal Stem Cells: Evidence of Prevascularisation Within 7 Days", European Cells and Materials vol. 26 2013 (pp. 49-65) (Year: 2013).*
International Search Report and Written Opinion for PCT/IL2015/050380 Completed Aug. 6, 2015; dated Aug. 9, 2015 12 Pages.
Wakitani et al. 2003 Embryonic stem cells injected into the mouse knee joint form teratomas and subsequently destroy the joint. Rheumatology, 42: 162-5.

(Continued)

*Primary Examiner* — Laura Schuberg
(74) *Attorney, Agent, or Firm* — The Roy Gross Law Firm, LLC; Roy Gross

(57) ABSTRACT

A composition including, (a) a mineral particle, (b) endothelial cells and mesenchymal cells, and (3) hyaluronic acid, is provided. Moreover, a kit which includes: a syringe, a mineral particle covered with endothelial cells and mesenchymal cells organized in 2 or more cell layers attached to the mineral particle, and hyaluronic acid, is also provided. Last, a method for filling a gap in a bone of a subject in need thereof, including contacting the gap with a composition of: (a) a mineral particle, (b) endothelial cells and mesenchymal cells, and (3) hyaluronic acid is provided.

15 Claims, 11 Drawing Sheets

(5 of 11 Drawing Sheet(s) Filed in Color)

(56) References Cited

U.S. PATENT DOCUMENTS

| | | | |
|---|---|---|---|
| 5,677,355 | A | 10/1997 | Shalaby |
| 5,686,091 | A | 11/1997 | Leong |
| 5,716,413 | A | 2/1998 | Walter |
| 5,716,616 | A | 2/1998 | Prockop |
| 5,755,792 | A | 5/1998 | Brekke |
| 5,769,899 | A | 6/1998 | Schwartz |
| 5,770,193 | A | 6/1998 | Vacanti |
| 5,824,084 | A | 10/1998 | Muschler |
| 6,049,026 | A | 4/2000 | Muschler |
| 6,200,606 | B1 | 3/2001 | Peterson |
| 6,333,029 | B1 | 12/2001 | Vyakarnam |
| 6,365,149 | B2 | 4/2002 | Vyakarnam |
| 6,534,084 | B1 | 3/2003 | Vyakarnam |
| 6,541,024 | B1 | 4/2003 | Kadiyala |
| 6,544,290 | B1 | 4/2003 | Lee |
| 6,811,776 | B2 | 11/2004 | Kale |
| 6,852,330 | B2 | 2/2005 | Bowman |
| 6,911,201 | B1 | 6/2005 | Merchav |
| 2003/0114936 | A1 | 6/2003 | Sherwood et al. |
| 2003/0149437 | A1 | 8/2003 | Livne et al. |
| 2004/0101960 | A1 | 5/2004 | Schaefer et al. |
| 2005/0074877 | A1 | 4/2005 | Mao |
| 2005/0177249 | A1 | 8/2005 | Kladakis et al. |
| 2007/0190101 | A1* | 8/2007 | Yang .................. A61L 27/50 424/423 |
| 2009/0074832 | A1 | 3/2009 | Zussman et al. |
| 2009/0104593 | A1* | 4/2009 | Werkmeister ........ C12N 5/0068 435/1.1 |
| 2011/0262404 | A1* | 10/2011 | Badoer ................ C12N 5/0663 424/93.7 |
| 2012/0003185 | A1 | 1/2012 | Meretzki |
| 2012/0028352 | A1* | 2/2012 | Oh .................... C12N 5/0606 435/366 |
| 2013/0116190 | A1* | 5/2013 | Pollock ................ A61K 31/728 514/17.2 |

FOREIGN PATENT DOCUMENTS

| | | | |
|---|---|---|---|
| WO | 2007115123 | A2 | 10/2007 |
| WO | 2008008229 | A2 | 1/2008 |
| WO | 2012103100 | A1 | 8/2012 |
| WO | WO 2012/134540 | * | 10/2012 |

OTHER PUBLICATIONS

Wang HS, et al. 2004 Mesenchymal stem cells in the Wharton's jelly of the human umbilical cord. Stem Cells. 22: 1330-7.

Werntz JR, Lane JM, Burstein AH, Justin R, Klein R, Tomin E. 1996 Qualitative and quantitative analysis of orthotopic bone regeneration by marrow. J Orthop Res. 14: 85-93.

Winston DJ, Ho WG, Champlin RE. 1990 Cytomegalovirus infections after allogeneic bone marrow transplantation. Rev Infect Dis. 12 Suppl 7: S776-92.

Koshikawa T, Ohgushi H. 1999 Autogenous cultured bone graft—bone reconstruction using tissue engineering approach. Ann Chir Gynaecol. 88:186-92.

Zuk PA, et al. 2001 Multilineage cells from human adipose tissue: implications for cell-based therapies. Tissue Eng. 7: 211-28.

Zuk PA, et al. 2002 Human adipose tissue is a source of multipotent stem cells. Mol Biol Cell. 13: 4279-95.

Zur Nieden NI, Kempka G, Ahr HJ. 2003 In vitro differentiation of embryonic stem cells into mineralized osteoblasts. Differentiation. 71: 18-27.

Schwartz et al. Ability of Commercial Demineralized Freeze-Dried Bone Allograft to Induce New Bone Formation. J Periodontol 1996; 67; 918-926.

Nilsson SK et al., "Cells capable of bone production engraft from whole bone marrow transplants in nonablated mice", J Exp Med., vol. 189, pp. 729-734 (Feb. 1999).

Fennema et al. The effect of bone marrow aspiration strategy on the yield and quality of human mesenchymal stem cells. Acta Orthopaedica 2009; 80 (5): 618-621.

Travlos. Normal Structure, Function, and Histology of the Bone Marrow. Toxicologic Pathology, 34:548-565, 2006.

Dominici M. et al; "Minimal criteria for defining multipotent mesenchymal stromal cells. The International Society for Cellular Therapy position statement"; Cytotherapy, vol. 8, No. 4, pp. 315-317, 2006.

Crockett J.C et al; "Bone remodelling at a glance"; Journal of Cell Science 124, pp. 991-998, 2011.

Bodine P.; "Wnt signaling control of bone cell apoptosis"; Cell Research 18, pp. 248-253, 2008.

Bohm A.M. et al; "Recruitment of osteogenic cells to bone formation sites during development and fracture repair" Neues aus der Forschung, 2016.

Lian J.B. et al; "Runx2/Cbfa1: A Multifunctional Regulator of Bone Formation"; Current Pharmaceutical Design, 9, pp. 2677-2685, 2003.

Srouji et al. Microscopy Analysis of Bone Marrow-Derived Osteoprogenitor Cells Cultured on Hydrogel 3-D Scaffold. Microscopy Research and Technique 66:132-138 (2005) (Year: 2005).

Birmingham et al. Osteogenic Differentiation of Mesenchymal Stem Cells is Regulated by Osteocyte and Osteoblast Cells in a Simplified Bone Niche. European Cell and Materials vol. 23, 3-27; 2012.

Aggarwal S, Pittenger MF. 2005 Human mesenchymal stem cells modulate allogeneic immune cell responses. Blood. 105:1815-22.

Bielby RC, Boccaccini AR, Polak JM, Buttery LD. 2004 In vitro differentiation and in vivo mineralization of osteogenic cells derived from human embryonic stem cells. Tissue Engineering, vol. 10, 9/10, p. 1518-1525.

Bruder SP, et al. 1998a The effect of implants loaded with autologous mesenchymal stem cells on the healing of canine segmental bone defects. J Bone Joint Surg Am.80:985-96.

Bruder SP, et al., 1998b Bone regeneration by implantation of purified, culture-expanded human mesenchymal stem cells. J Orthop Res. 16:155-62.

Buttery LD, et al. 2001 Differentiation of osteoblasts and in vitro bone formation from murine embryonic stem cells. Tissue Eng. 7:89-99.

Chakrabarti S, et al., 2002 Adenovirus infections following allogeneic stem cell transplantation. Blood, 100:1619-27.

Chakrabarti S, et al., 2004. Adenovirus Infections in Stem Cell Transplant Recipients. Leukemia & Lymphoma, vol. 45 (5), pp. 873-885.

Choi K, Kennedy M, Kazarov A, Papadimitriou JC, Keller G. 1998 A common precursor for hematopoietic and endothelial cells. Development 125:725-32.

Cinotti G, et al., 2004 Experimental posterolateral spinal fusion with porous ceramics and mesenchymal stem cells. J Bone Joint Surg Br. 86: 135-42.

Cohen Y, Nagler A. 2004 Umbilical cord blood transplantation—how, when and for whom? Blood Rev. 18:167-79.

Gang EJ,et al., 2004 In vitro mesengenic potential of human umbilical cord blood-derived mesenchymal stem cells. Biochem Biophys Res Commun 321: 102-8.

Gerasimov et al.,1986 Differentiation potentials of clonal strains of bone marrow fibroblasts. Biull Eksp Bioi Med. I0I:717-9.

Gotoh Y, Hiraiwa K, Nagayama M. 1990 In vitro mineralization of osteoblastic cells derived from human bone.Bone Miner. 8: 239-50.

Hamaguchi et al.,1999 In vitro hematopoietic and endothelial cell development from cells expressing TEK receptor in murine aorta-gonad-mesonephros region. Blood 93: 1549-56.

He Z, Huang S, Li Y, Zhang Q. 2002 Human embryonic stem cell lines preliminarily established in China. Zhonghua Yi Xue Za Zhi. 82: 1314-8.

Hofmann GO, et al.,1998 Bridging long bone and joint defects with allogeneic vascularized transplants.Langenbecks Arch Chir Suppl Kongressbd. 115: 1285-7.

Horwitz et al.,1999 Transplantability and therapeutic effects of bone marrow-derived mesenchymal cells in children with osteogenesis imperfecta. Nat Med. 5: 309-13.

Horwitz et al. 2001 Clinical responses to bone marrow transplantation in children with severe osteogenesis imperfecta. Blood. 97: 1227-31.

(56) References Cited

OTHER PUBLICATIONS

Horwitz et al. 2002 Isolated allogeneic bone marrow-derived mesenchymal cells engraft and stimulate growth in children with osteogenesis imperfect. PNAS. 99: 8932-7.

Hovatta et al. 2003 A culture system using human foreskin fibroblasts as feeder cells allows production of human embryonic stem cells. Hum Reprod. 18: 1404-9.

Jaiswal et al., 1997 Osteogenic differentiation of purified, culture-expanded human mesenchymal stem cells in vitro.1. Cell Biochem. 64: 295-312.

Johnson DR. 2000 Differential expression of human major histocompatibility class I loci: HLA-A,-B,and-C.Hum Immunol. 61: 389-96.

Kadiyala S,et al. 1997 Culture expanded canine mesenchymal stem cells possess osteochondrogenic potential in vivo and in vitro. Cell Transplant. 6: 125-34.

Kawaguchi H,et al. 2004 Enhancement of periodontal tissue regeneration by transplantation of bone marrow mesenchymal stem cells. 1 Periodontol. 75: 1281-7.

Koc et al. 1999 Bone marrow-derived mesenchymal stem cells remain host-derived despite successful hematopoietic engraftment. Exp Hematol. 27: 1675-81.

Krampera et al. 2003 Bone marrow mesenchymal stem cells inhibit the response of naive and memory antigen-specific T cells to their cognate peptide. Blood 101: 3722-9.

Lane et al. 1999 Bone marrow and recombinant human bone morphogenetic protein-2 in osseous repair. Clin Orthop. 361: 216-27.

Lee OK ,Kuo TK, Chen WM, Lee KD, Hsieh SL, Chen TH. 2004 Isolation of multipotent mesenchymal stem cells from umbilical cord blood. Blood. 103: 1669-75.

Lee WY et al. 2002 The effect of bone marrow transplantation on the osteoblastic differentiation of human bone marrow stromal cells. J Clin Endocrinol Metab. 87: 329-35.

Lewandrowski et al. 2000 Bioresorbable bone graft substitutes of different osteoconductivities. Biomaterials. 21: 757-64.

Maitra B et al. 2004 Human mesenchymal stem cells support unrelated donor hematopoietic stem cells and suppress T-cell activation. Bone Marrow Transplant 33: 597-604.

Mitchell KE, et al. 2003 Matrix cells from Wharton's jelly form neurons and glia. Stem Cells. 21: 50-60.

Mizuno H, Hyakusoku H. 2003 Mesengenic potential and future clinical perspective of human processed lipoaspirate cells. J Nippon Med Sch. 70: 300-6.

Murohara T,et al. 2000 Transplanted cord blood-derived endothelial precursor cells augment postnatal neovascularization. J Clin Invest. 105: 1527-36.

Nade S,et al. 1983 Osteogenesis after bone and bone marrow transplantation. Clin Orthop Relat Res. 181: 255-63.

Neppert J, Nunez G, Stastny P. 1984 HLA-A, B, C; -DR; -MT, -MB, and SB antigens on unstimulated human endothelial cells. Tissue Antigens. 24: 40-7.

Niemeyer P,et al. 2004 Allogenic transplantation of human mesenchymalstem cells for tissue engineering purposes:an in vitro study. Orthopade. 33: 1346-53.

Ohgushi et al. 1990 Marrow cell induced osteogenesis in porous hydroxyapatite and tricalcium phosphate. J Biomed Mater Res. 24: 1563-70.

Pereira et al. 1995 Cultured adherent cells from marrow can serve as long-lasting precursor cells for bone, cartilage, and lung in irradiated mice. PNAS, 92: 4857-61.

Petersen BE, et al. 1999 Bone marrow as a potential source of hepatic oval cells. Science. 284: 1168-70.

Ringe J, et al. 2002 Porcine mesenchymal stem cells. Induction of distinct mesenchymal cell lineages. Cell Tissue Res. 307: 321-7.

Schmidt et al. 1991 A randomized, controlled trial of prophylactic ganciclovir for cytomegalovirus pulmonary infection; N Engl J Med. 1991, 324: 1005-11.

Shahgasempour et al. 1998 Modulation of HLA class I antigen and ICAM-2 on endothelial cells after in vitro infection with human cytomegalovirus. Immunol Cell Biol. 76: 217-21.

Shang Q,et al. 2001 Tissue-engineered bone repair of sheep cranial defects with autologous bone marrow stromal cells. J Craniofac Surg. 12: 586-93.

Sottile V, Thomson A, McWhir J. 2003 In vitro osteogenic differentiation of human ES cells. Cloning Stem Cells. 5: 149-55.

Sun S, Guo Z, Xiao X, Liu B, Liu X, Tang PH, Mao N. 2003 Isolation of mouse marrow mesenchymal progenitors by a novel and reliable method. Stem Cells. 21: 527-35.

Theunissen et al. 2005 A multifactorial analysis of umbilical cord blood, adult bone marrow and mobilized peripheral blood progenitors. Exp Hem. 33: 165-72.

Valimaki et al. 1999 A prospective study of bone loss and turnover after allogeneic bone marrow transplantation. Bone Marrow Transplant. 23: 355-61.

\* cited by examiner

Scaffold only
17  #18  #30
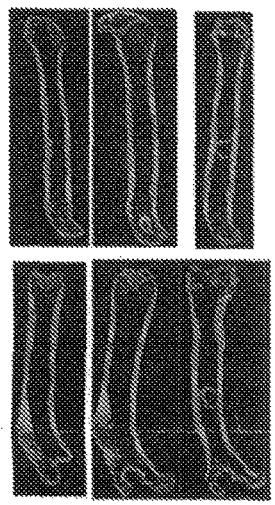
Scaffold + 3 million cells
7  #8  #9  #10  #11
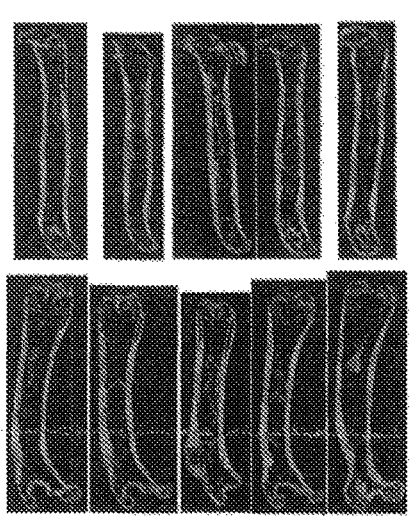
Scaffold + 5 million Cells
26  #27  #28  #29
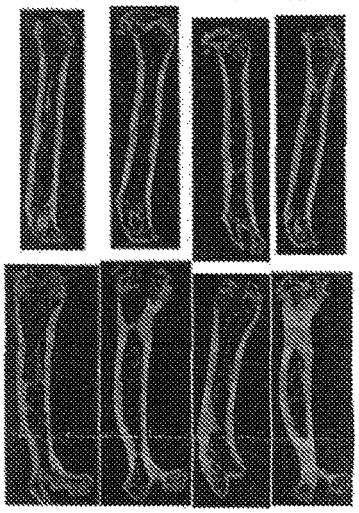
FIG. 3A
FIG. 3C
FIG. 3E
17  #18
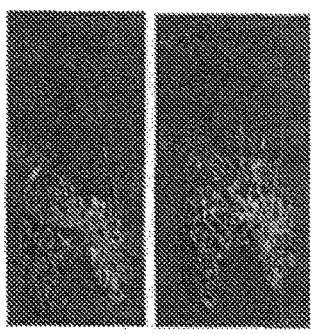
30
7  #8  #9
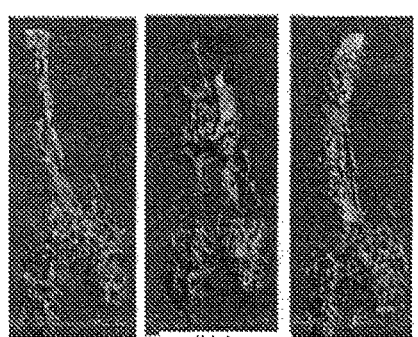
10  #11
26  #27
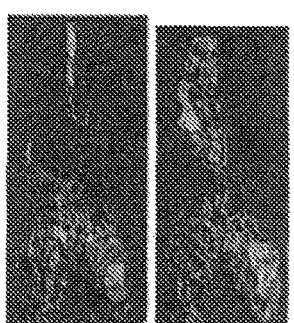
28  #29
FIG. 3B
FIG. 3D
FIG. 3F

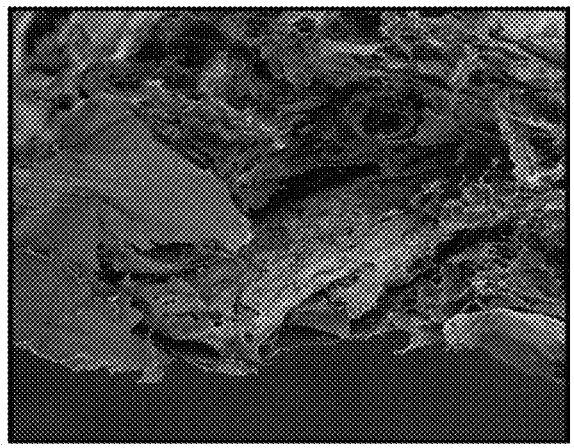 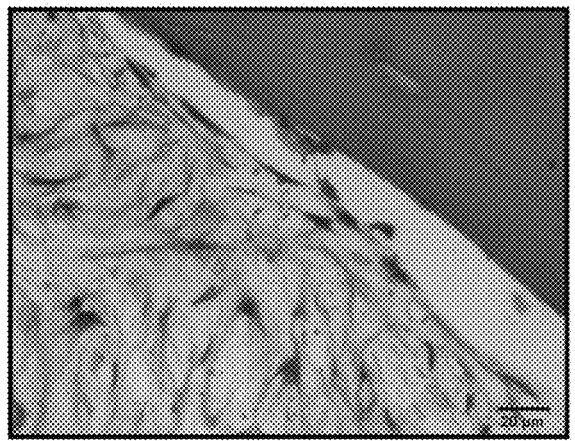
FIG. 10A                    FIG. 10B
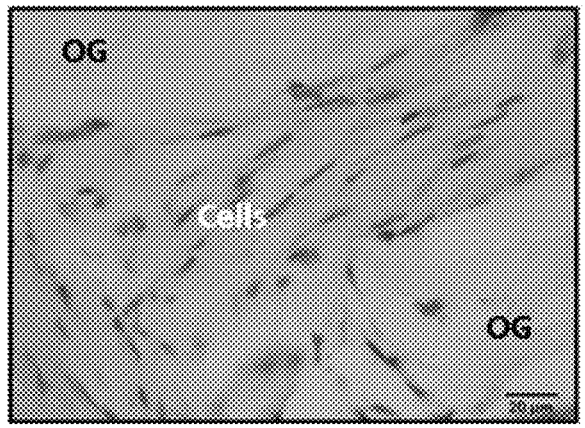 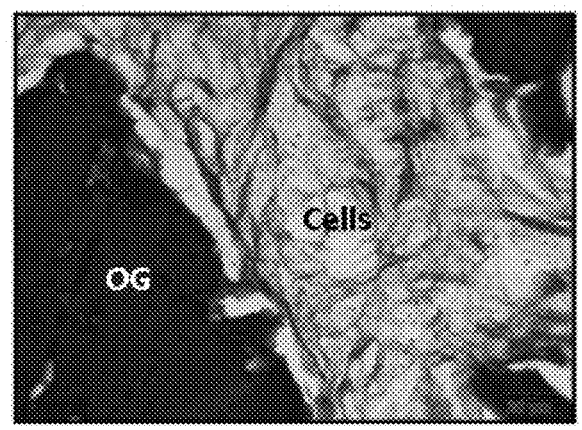
FIG. 10C                    FIG. 10D

BONE REPAIR COMPOSITIONS

RELATED APPLICATIONS

This application is a National Phase of PCT Patent Application No. PCT/IL2015/050380 having International filing date of Apr. 9, 2015, which claims the benefit of priority of U.S. Provisional Patent Application No. 61/977,691 filed on Apr. 10, 2014. The contents of the above applications are all incorporated by reference as if fully set forth herein in their entirety.

FIELD OF INVENTION

The present invention relates to the field of bone, cartilage and hard tissue prosthetics, and more particularly to the use of cellular-based implants for the preparation of prosthetic implants for bone replacement and repair.

BACKGROUND OF THE INVENTION

The repair of outsized deficiencies, typically defined as gaps of at least about 2.4 mm in size, in the diaphyseal, craniomaxillofacial and other skeletal bones is a considerable problem in orthopedic surgery.

In 1998, about 300,000 bone-graft procedures were performed in the United States alone. This number increased to approximately 450,000 by the year of 2000, when the number of bone grafting procedures performed worldwide exceeded 2.2 million (Lewandrowski et al, 2000). Of the 300,000 procedures performed in 1998, 90% involved the use of either autologous grafts (i.e. using tissue from another part of the body of the patient), or of allografts (i.e. using tissue from a live human donor or cadaver). Therefore, a phase of tissue harvest from the patient or from a donor is required.

The tissue harvesting is executed by a surgical procedure usually involved collecting tissue from the iliac crest, the distal femur, the proximal tibia, the fibula, or from other small bones. The harvested tissue is restructured and transplanted at the damaged site.

However, the graft-harvesting procedures are associated with considerable morbidity and substantial pain. Tissue harvesting for an autologous grafts or from live donors for an allograft may also result in complications such as inflammation, infection, or even death.

The limited supply and inherited harvesting complications have inspired the development of alternative strategies for the repair of significant bone defects.

The use of 3-dimensional (3-D) bone substitutes such as bone extract, polymer or mineral scaffolds as implants has been investigated and porous biocompatible scaffolds have been used for the repair and regeneration of bone tissue.

Early attempts at tissue repair have focused mainly on the use of amorphous, biocompatible foam as porous plugs to fill large voids in bone. U.S. Pat. No. 4,186,448 described the use of porous mesh plugs composed of polyhydroxy acid polymers, such as polylactide, for healing bone voids. Several different methods for making other scaffolds were also described (i.e. U.S. Pat. Nos. 5,133,755; 5,514,378; 5,522,895; 5,607,474; 5,677,355; 5,686,091; 5,716,413; 5,755,792; 5,769,899; 5,770,193; 6,333,029; 6,365,149 and 6,534,084).

Bone marrow (BM) has been shown to contain population of cells that possess osteogenic potential. As such, an alternative to the scaffold-osteoinductive approach is to transplant into patients living cells that possess this capacity. Cytokine-manipulated, naïve autologous and allogeneic BM cells have successfully healed diffracted or resorbed bones in experimental models (Werntz et al, 1996; Lane et al, 1999; Nilsson et al, 1999; Kawaguchi et al, 2004) and human patients (Horwitz et al, 1999; Horwitz et al 2001, 2004). Progenitor cells of the osteogenic lineage are seeded onto biocompatible (biodegradable or non-biodegradable) scaffolds in the presence or absence of growth promoting factors (U.S. Pat. Nos. 6,541,024; 6,544,290; 6,852,330). Transplantation into affected patients is performed following an ex-vivo expansion phase of the cells on the given scaffold. Using this approach, either primary osteogenic cells or expanded Mesenchymal Stromal Cells (MSC) layered upon ceramic scaffolds was able to regenerate bone tissue (Kadiyala et al, 1997; Bruder et al, 1998a,b; Cinotti et al, 2004).

Living bone is a continuously evolving organ and in the normal course of bone maintenance, a constant remodeling process is being employed. In those procedures, Old bone is being replaced by new bone and the organ responds to its environment changing requirements for strength and elasticity. Therefore, normal remodeling progression requires that the mechanical loading processes of bone resorption and bone formation procedures are tightly coordinated.

In cellular terms, this depends on sequential functioning of osteoclasts (bone resorbing cells) and osteoblasts (bone forming cells). In addition, endothelial cell and endothelial cell precursors (angioblasts) are required to form the new blood vessels in the developed bone tissue. Yet, the various cell types participating in bone formation are of different lineages. It is now known that osteoblasts stalk from mesenchymal stem cells, while osteoclasts (directly originating from Hematopoietic Stem Cells (HSC)) and endothelial cells are descendents of a common blast colony-forming cell (Choi et al, 1998; Hamaguchi et al, 1999). As such, methodologies for ex-vivo production of bone-like material that rely on osteoblasts as the exclusive cellular component suffer from an inherited fault.

SUMMARY OF THE INVENTION

In one embodiment, the present invention provides a composition comprising, (a) a mineral particle, (b) endothelial cells and mesenchymal cells, and (3) hyaluronic acid. In another embodiment, the present invention provides a composition comprising, (a) a mineral particle, (b) adipose derived cells comprising mesenchymal stem cells and/or osteoprogenitor cells and (3) hyaluronic acid.

In another embodiment, the present invention provides a kit comprising: a syringe, a mineral particle comprising endothelial cells and mesenchymal cells organized in 2 or more cell layers attached thereto, and hyaluronic acid.

In another embodiment, the present invention provides a method for filling a gap in a bone of a subject in need thereof, comprising the step of contacting the gap with a composition comprising: (a) a mineral particle, (b) endothelial cells and mesenchymal cells, and (3) hyaluronic acid, thereby filling a gap in a bone of a subject in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 are MicroCT scan micrographs of treated legs 16 weeks post injection: (A, B) Treated legs of scaffold only group. (C, D) Treated leg of scaffold (mineral particle) and 3 million Adipose Tissue derived Cells. (E, F) Treated legs of scaffold (mineral particle) and 5 million Adipose Tissue derived Cells.

FIG. 10 are micrographs showing scanning electron microscope and histological analysis of the adipose tissue derived cells cultivated on bone mineral particles (OG). (A) SEM (B) Hematoxiline & Eosin stain (C) Toluidine blue stain (D) Picro Sirius Red stain.

DETAILED DESCRIPTION OF THE INVENTION

Figure 1:
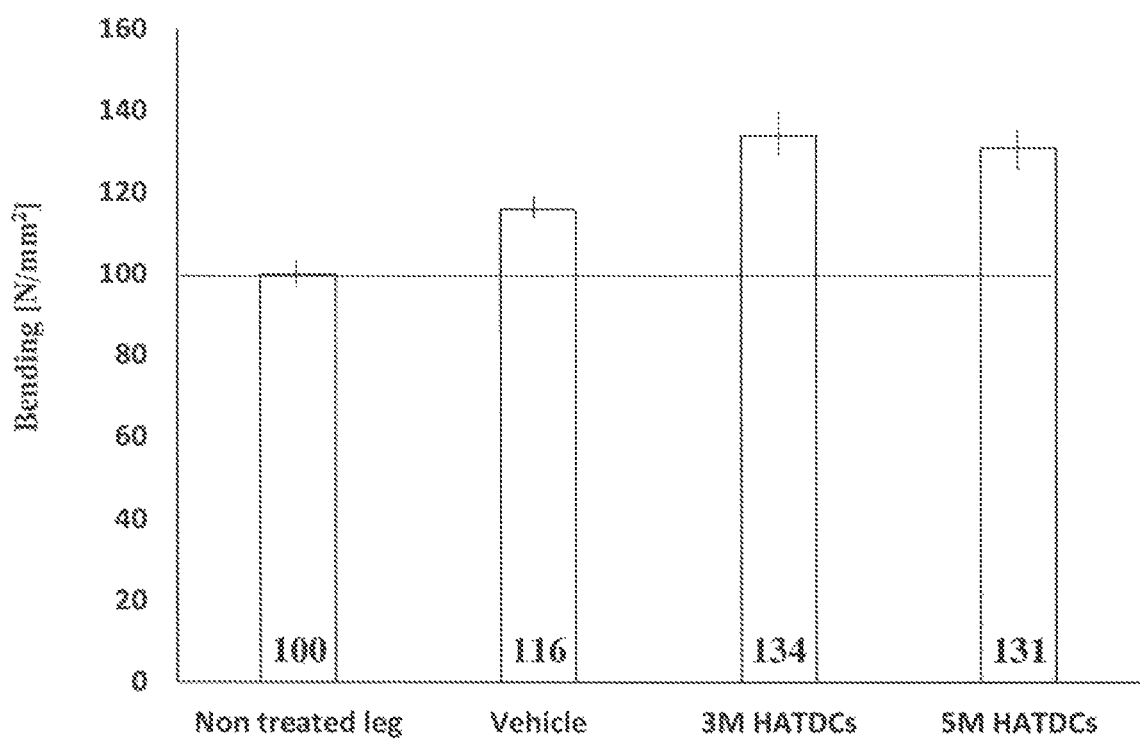
FIG. 1 is a bar graph showing the Average σ bending of rat femur bones 8 weeks after injection. Results are expressed as mean±SEM.

The present invention, in some embodiments, provides a novel solution for the ex-vivo regeneration of remodeled bone, cartilage and other hard tissue applications. The background art describes bone substitutes made from cells of osteogenic lineage cultured on a scaffold. In contrast with this art, the present invention manipulates co-culture and multi-cell cultures made up of two or more independent cell types grown as multi-layered cell culture on mineral particles as scaffolds to optimize the bone regeneration and remodeling processes. In some embodiments, multi-layered cell culture is obtained by growing the culture in a flow system at a high density. In some embodiments, cells within one layer are in communication with cells within a second layer.

Multi-Layer Cell Culture

In some embodiments, a multi-layered cell culture is a heterogeneous cell culture composed of at least two cell types. In another embodiment, a multi-layered cell culture is a heterogeneous cell culture composed of at least three cell types. In another embodiment, a multi-layered cell culture is a heterogeneous cell culture composed of at least four cell types. In another embodiment, a multi-layered cell culture comprises mesenchymal cells. In another embodiment, a multi-layered cell culture comprises osteogenic cells. In another embodiment, a multi-layered cell culture comprises osteoprogenitor cells.

In another embodiment, a multi-layered cell culture comprises a bottom layer of cells and a top layer of cells. In another embodiment, a multi-layered cell culture comprises a bottom layer of cells, a middle layer of cells and a top layer of cells. In another embodiment, a multi-layered cell culture is a 3D cell culture (as opposed to a single layer of cells that is termed a 2D cell culture). In another embodiment, a 3D cell culture consists cells and extra cellular matrix. In another embodiment, a 3D cell culture consists cells and extra cellular matrix. In another embodiment, a 3D cell culture is grown on the surface of a mineral particle as described herein. In another embodiment, a 3D cell culture consists a biotic matter. In another embodiment, a 3D cell culture of 2 or more cell layers is attached to the mineral particle. In another embodiment, a 3D cell culture of 2 or more cell layers is operably attached to the mineral particle.

In some embodiments, a multi-layered cell culture or a 3D cell culture includes at least 2 layers of cells, wherein at least 10% of the cells in one layer are in contact with at least 10% of the cells in another layer. In some embodiments, a multi-layered cell culture or a 3D cell culture includes at least 3 layers of cells.

In some embodiments, at least 10% of the cells in one layer within a multi-layered cell culture or a 3D cell culture are in contact with at least 10% of the cells in another layer within the same multi-layered cell culture or 3D cell culture. In some embodiments, at least 20% of the cells in one layer within a multi-layered cell culture or a 3D cell culture are in contact with at least 20% of the cells in another layer within the same multi-layered cell culture or 3D cell culture. In some embodiments, at least 30% of the cells in one layer within a multi-layered cell culture or a 3D cell culture are in contact with at least 30% of the cells in another layer within the same multi-layered cell culture or 3D cell culture. In some embodiments, at least 40% of the cells in one layer within a multi-layered cell culture or a 3D cell culture are in contact with at least 40% of the cells in another layer within the same multi-layered cell culture or 3D cell culture. In some embodiments, at least 50% of the cells in one layer within a multi-layered cell culture or a 3D cell culture are in contact with at least 50% of the cells in another layer within the same multi-layered cell culture or 3D cell culture. In some embodiments, at least 60% of the cells in one layer within a multi-layered cell culture or a 3D cell culture are in contact with at least 60% of the cells in another layer within the same multi-layered cell culture or 3D cell culture. In another embodiment, the phrase "in contact" is in physical contact. In another embodiment, the phrase "in contact" is in cell to cell interaction.

In another embodiment, the phrase "3D culture (three dimensional culture)" refers to a culture in which the cells are disposed to conditions which are compatible with cell growth while allowing the cells to grow in more than one layer. In another embodiment, cells within the 3D cell culture are held in a complex network of extra cellular matrix nanoscale fibers that allows the establishment of various local microenvironments. In another embodiment, extra cellular ligands within the ECM mediate not only the attachment to the basal membrane but also access to a variety of vascular and lymphatic vessels. In another embodiment, cells within the 3D cell culture are exposed to oxygen, hormones and nutrients. In another embodiment, a 3D cell culture is characterized by cell-cell and cell-ECM interactions.

The Cells

In another embodiment, the invention provides a composition comprising, (a) a mineral particle, (b) endothelial cells and mesenchymal cells, and (c) hyaluronic acid. In another embodiment, the invention provides a composition comprising, (a) a mineral particle, (b) a 3D cell culture, and (c) hyaluronic acid. In another embodiment, the invention provides a composition comprising, (a) a mineral particle, (b) osteoprogenitor cells and (c) hyaluronic acid. In another embodiment, a 3D cell culture comprises endothelial cells and mesenchymal cells. In another embodiment, a 3D cell culture comprises adipose tissue derived cells. In another embodiment, adipose tissue derived cells comprise adipose-derived stem cells (ASC) (CD34− CD45− CD11b−, CD19, HLA-DR−, CD105+, CD73+, CD90+). In another embodiment, adipose tissue derived cells comprise endothelial progenitor cells (CD31+ CD34+ CD45− CD144+ CD146+ CD102+). In another embodiment, adipose tissue derived cells comprise mature endothelial cells (CD31+ CD34+ CD45− CD90− CD144+ CD146+ CD105+). In another embodiment, adipose tissue derived cells comprise vascular smooth muscle cells (Smooth muscle alpha-actin positive, Desmin positive, h-caldesmon positive, Smooth muscle myosin heavy chain positive). In another embodiment, adipose tissue derived cells comprise cells capable of differentiating into adipogenic and osteogenic cells. In another embodiment, a 3D cell culture comprises: osteoprogenitor cells, osteoblasts, osteocytes, chondroblasts, chondrocytes, osteoclasts, or any combination thereof. In another embodiment, mesenchymal cells are mesenchymal stem cells. In another embodiment, mesenchymal cells comprise mesenchymal stem cells and/or osteoprogenitor cells. In another embodiment, a 3D cell culture comprises Hematopoietic CD34+ cells. In another embodiment, a 3D cell culture comprises osteoprogenitor cells. In another embodiment, adipose derived cells comprise endothelial cells, mesenchymal cells, mesenchymal stem cells, or any combination thereof.

In another embodiment, Adipose derived cells were obtained from adipose tissue (such as of liposuction procedures). In another embodiment, endothelial cells were collected from peripheral blood. In another embodiment, cells of the invention are maintained and grown at 37° C. in a tissue culture incubator under humidified condition with 5% $CO_2$ In another embodiment, mineral particles carrying a multi-layered heterogeneous cell culture are subjected to osteogenic culture differentiation conditions comprising: osteogenic culture differentiation medium composed of one or more of the following molecules in preferred concentration: dexamethasone (10-200 nM) (Sigma), sodium .beta.-glycerophosphate (5-25 mM) (Sigma), 1,25 dihydroxycholecalciferol (calcitriol: 1-50 nM) (Sigma), L-ascorbic acid-2-phosphate (0.05-500 mM) (Sigma) and BMP-2 (10 ng/ml-10 ug/ml).

In another embodiment, mineral particles carrying a multi-layered heterogeneous cell culture are subjected to Chondrocyte differentiation conditions comprising: medium with chondrogenic cocktail: DMEM HG, BMP-6 [500 ng/ml] (Sigma), TGF-b3 [10 ng/ml] (Sigma), ITS and pre-mix [dil. :20 of the dil. Stock(:100)] (Sigma), Dexamethasone [100 nM] (Sigma), L-ascorbic acid 2-phosphate [50 mg/ml] (Sigma), Sodium pyruvate [100 mg/ml] (Sigma), Proline [40 mg/ml] (Sigma), Pen/Strep/Nys 1%, Glutamine 1%.

In another embodiment, a multi-layered heterogeneous cell culture comprises at least two cell types selected from the group consisting of: osteoprogenitor cells, osteoblasts, mesenchymal cells, embryonic mesenchymal cells, osteoclasts, osteocytes, hematopoietic progenitor cells, chondrocytes, chondroblasts and endothelial cells. In another embodiment, cells as described herein are derived from mesenchymal stem cells and/or osteoprogenitor cells. In another embodiment, cells as described herein are derived from an autologous source, a syngeneic source and an allogeneic source. In another embodiment, cells as described herein are derived from bone marrow, placenta, adipose tissue, cord blood, peripheral blood, mobilized peripheral blood, embryonic stem cells, or any combination thereof.

Cell Density

In another embodiment, a composition as described comprises at least $1 \times 10^2$ cells as described herein per 1 mg of mineral particle. In another embodiment, a composition as described comprises at least $1 \times 10^3$ cells as described herein per 1 mg of mineral particle. In another embodiment, a composition as described comprises at least $1 \times 10^2$ to $1 \times 10^6$ cells as described herein per 1 mg of mineral particle. In another embodiment, a composition as described comprises at least $1 \times 10^2$ to $1 \times 10^4$ cells as described herein per 1 mg of mineral particle. In another embodiment, a composition as described comprises at least $5 \times 10^2$ to $5 \times 10^4$ cells as described herein per 1 mg of mineral particle.

In another embodiment, a composition consisting particles and cells include 2% to 60% v/v cells as described herein. In another embodiment, a composition consisting particles and cells include 20% to 60% v/v cells as described herein. In another embodiment, a composition consisting particles and cells include 2% to 10% v/v cells as described herein. In another embodiment, a composition consisting particles and cells include 20% to 40% v/v cells as described herein. In another embodiment, a composition consisting particles and cells include 30% to 75% v/v cells as described herein. In another embodiment, a composition consisting particles and cells include 40% to 80% v/v cells as described herein.

Biotic Components

In another embodiment, the invention provides that the composition further comprises albumin. In another embodiment, the invention provides that the composition further comprises an extra-cellular matrix (ECM) protein. In another embodiment, the invention provides that the composition further comprises fibrin. In another embodiment, the invention provides that the composition further comprises fibronectin. In another embodiment, the invention provides that the composition further comprises collagen type I. In another embodiment, the invention provides that the composition further comprises laminin. In another embodiment, the invention provides that the composition further comprises vitronectin.

In another embodiment, the invention provides that the composition further comprises a bone morphogenetic protein. In another embodiment, the invention provides that the composition further comprises insulin like growth factor. In another embodiment, the invention provides that the composition further comprises interleukin-1, interleukin-6, a tumor necrosis factor, RANKL, or any combination thereof. In another embodiment, a composition includes an autologous multicellular 3D cell culture suspended in Human Serum Albumin (HSA) containing medium. In another embodiment, a composition as described herein further comprises an anti-inflammatory agent. In another embodiment, a composition as described herein further comprises an antibiotic.

In another embodiment, the invention provides that the composition further comprises a biocompatible binder. In another embodiment, the biocompatible binder are one or more selected from the group consisting of fibrin adhesive, fibrinogen, thrombin, mussel adhesive protein, silk, elastin, collagen, casein, gelatin, albumin, keratin, chitin and chitosan. In another embodiment, the biocompatible binder are one or more selected from the group consisting of starch, polylactic acid, polyglycolic acid, polylactic-co-glycolic acid, polydioxanone, polycaprolactone, polycarbonate, polyoxoester, polyamino acid, poly-anhydride, polyhydroxybutylate, polyhydroxyvalerate, poly(propylene glycol-co-fumaric acid), tyrosine-based-polycarbonate, polyvinylpyrrolidone, cellulose, ethyl cellulose and carboxy methyl cellulose.

In another embodiment, the invention provides that the composition further comprises vitamins. In another embodiment, the invention provides that the composition further comprises a glucosamine. In another embodiment, the invention provides that the composition further comprises a cytokine. In another embodiment, the invention provides that the composition further comprises growth factors.

Biocompatible Polymer for Suspending Cells

In another embodiment, the invention provides that the composition comprises mineral particles and cells deposited or attached to the mineral particles wherein the particles carrying the cells are suspended in cell culture media comprising biocompatible polymer, or a mixture of cell culture media and biocompatible polymer. The biocompatible polymers can be a natural polymer or a synthetic polymer. The phrase "synthetic polymer" refers to polymers that are not found in nature, even if the polymers are made from naturally occurring biomaterials. Examples include, but are not limited to, aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Naturally occurring biocompatible polymerinclude include, but are not limited to, fibrinogen, fibrin, thrombin, chitosan, collagen, alginate, poly(N-isopropylacrylamide), hyaluronate, albumin, collagen, synthetic polyamino acids, prolamines, polysaccharides such as alginate, heparin, and other naturally occurring biodegradable polymers of sugar units. In another embodiment, ionic hydrogels may be used, for example, ionic polysaccharides, such as alginates or chitosan. Ionic hydrogels may be produced by cross-linking the anionic salt of alginic acid, a carbohydrate polymer isolated from seaweed, with ions, such as calcium cations.

In another embodiment, biocompatible polymer for suspending cells deposited or attached to the mineral particles, is a water-soluble. In another embodiment, biocompatible polymer for suspending cells deposited or attached to the mineral particles is a gel.

In another embodiment, the biocompatible polymer is characterized as a viscous substance. Viscous materials resist shear flow and strain linearly with time when a stress is applied. The viscosity of a solution comprising biocompatible polymer can be higher by 10%, by 20%, by 50%, by 80%, or by 100% of that of an aqueous medium not comprising biocompatible polymer, and can be even 3-folds, 4-folds, 5-folds, 10-folds, 20-folds, 30-folds, 50-folds, 60-folds, 60-folds and even 100-folds or 1000-folds higher.

Exemplary biocompatible polymers that are suitable for use in the context of embodiments of the present invention are polysaccharides. The term "polysaccharide" as used herein is meant to include compounds composed of 10 saccharide units and up to hundreds and even thousands of monosaccharide units per molecule, which are held together by glycoside bonds and range in their molecular weights from around 5,000 and up to millions of Daltons.

In another embodiment, the polysaccharide is a glycosaminoglycan (GAG). In another embodiment, the GAG is Hyaluronic acid (HA), as described hereinbelow. HA is a high molecular weight unsulfated glycosaminoglycan (GAG), composed of repeating disaccharide units composed of (P-1,4)-linked D-glucuronic acid and (P-1,3)-linked N-acetyl-D-glucosamine.

Additional suitable polysaccharides include, but are not limited to, agar, alginate, laminarin and pectin, as long as these polymers exhibit the desired physical characteristic.

In another embodiment, the biocompatible polymer comprises at least 50% porosity. In another embodiment, the biocompatible polymer comprises at least 60% porosity. In another embodiment, the biocompatible polymer comprises at least 70% porosity. In another embodiment, the biocompatible polymer comprises at least 75% porosity. In another embodiment, the biocompatible polymer comprises at least 80% porosity. In another embodiment, the biocompatible polymer comprises at least 85% porosity. In another embodiment, the biocompatible polymer comprises at least 90% porosity. In another embodiment, the biocompatible polymer comprises at least 92% porosity. In another embodiment, a porous sponge comprises at least 95% porosity.

In another embodiment, the biocompatible polymer comprises pores having a diameter of at least 100 µm. In another embodiment, the biocompatible polymer comprises pores having a diameter of at least 120 µm. In another embodiment, the biocompatible polymer comprises pores having a diameter of at least 150 µm. In another embodiment, the biocompatible polymer comprises pores having a diameter of 100-900 µm. In another embodiment, the biocompatible polymer comprises pores having a diameter of 120-900 µm. In another embodiment, the biocompatible polymer comprises pores having a diameter of 120-850 µm. In another embodiment, the biocompatible polymer comprises pores having a diameter of 150-800 µm. In another embodiment, the biocompatible polymer comprises pores having a diameter of 200-800 μm. In another embodiment, the biocompatible polymer comprises pores having a diameter of 220-750 μm.

In another embodiment, the porosity of the scaffold (e.g., comprising the mineral particle) is controlled by a variety of techniques known to those skilled in the art. In another embodiment, as the porosity is increased, use of polymers having a higher modulus, addition of suffer polymers as a co-polymer or mixture, or an increase in the cross-link density of the polymer are used to increase the stability of the scaffold with respect to cellular contraction.

In another embodiment, the choice of polymer and the ratio of polymers in a co-polymer scaffold of the invention is adjusted to optimize the stiffness/porosity of the scaffold. In another embodiment, the molecular weight and cross-link density of the scaffold is regulated to control both the mechanical properties of the scaffold and the degradation rate (for degradable scaffolds). In another embodiment, the mechanical properties are optimized to mimic those of the tissue at the implant site. In another embodiment, the shape and size of the final scaffold are adapted for the implant site. In another embodiment, scaffold materials comprise natural or synthetic organic polymers that can be gelled, or polymerized or solidified (e.g., by aggregation, coagulation, hydrophobic interactions, or cross-linking) into a 3-D open-lattice structure that entraps water and/or other molecules, e.g., to form a hydrogel.

In another embodiment, the choice of polymer and the ratio of polymers in a co-polymer scaffold of the invention is adjusted to optimize the stiffness/porosity of the scaffold. In another embodiment, the molecular weight and cross-link density of the scaffold is regulated to control both the mechanical properties of the scaffold and the degradation rate (for degradable scaffolds). In another embodiment, the mechanical properties are optimized to mimic those of the tissue at the implant site. In another embodiment, the shape and size of the final scaffold are adapted for the implant site. In another embodiment, scaffold materials comprise natural or synthetic organic polymers that can be gelled, or polymerized or solidified (e.g., by aggregation, coagulation, hydrophobic interactions, or cross-linking) into a 3-D open-lattice structure that entraps water and/or other molecules, e.g., to form a hydrogel.

In another embodiment, polymers used in scaffold material compositions are biocompatible, biodegradable and/or bioerodible and act as adhesive substrates for cells. In another embodiment, the structural scaffold materials are non-resorbing or non-biodegradable polymers or materials. The phrase "non-biodegradable polymer", as used herein, refers to a polymer or polymers which at least substantially (i.e. more than 50%) do not degrade or erode in-vivo. The terms "non-biodegradable" and "non-resorbing" are equivalent and are used interchangeably herein.

In another embodiment, the phrase "biodegradable polymer" as used herein, refers to a polymer or polymers which degrade in-vivo, and wherein erosion of the polymer or polymers over time occurs concurrent with or subsequent to release of cells/tissue. The terms "biodegradable" and "bioerodible" are equivalent and are used interchangeably herein.

Hyaluronic Acid

In another embodiment, the invention provides that the composition comprises mineral particles and cells deposited or attached to the mineral particles wherein the particles carrying the cells are suspended in cell culture media, hyaluronic acid, or a mixture of cell culture media and hyaluronic acid. In another embodiment, the term "hyaluronic acid (HA)" is synonymous with hyaluronan or sodium hyaluronate. In another embodiment, hyaluronic acid is within a composition comprising a physiological buffer. In another embodiment, hyaluronic acid has a molecular weight of 200,000 to 850,000 daltons.

The term "HA" is also meant to include its pure or salt form, and also all cross-linked, modified or hybrid forms of HA. Cross-linker agents for HA operating via the carboxylic groups or via the amine groups following HA deacetylation include, but are not limited to, aldehydes (e.g., Glutaraldehyde), Dialdehydes, Genipin, Cinnamic acid, or derivatives thereof. Hybrid forms of HA include, without limitation, a protein or a carbohydrate polymer with HA, such as, diphenylalanin HA, Albumin HA, Fibrinogen HA, fibrin HA, and Chitosan HA.

In another embodiment, Hyaluronic acid composition for suspending cells deposited or attached to the mineral particles is a composition comprising from 0.5 mg to 50 mg Hyaluronic acid per 1 mL of solution (comprising a buffer). In another embodiment, Hyaluronic acid composition for suspending cells deposited or attached to the mineral particles is a composition comprising from 0.5 mg to 5 mg Hyaluronic acid per 1 mL of solution (comprising a buffer). In another embodiment, Hyaluronic acid composition for suspending cells deposited or attached to the mineral particles is a composition comprising from 5 mg to 20 mg Hyaluronic acid per 1 mL of solution (comprising a buffer). In another embodiment, Hyaluronic acid composition for suspending cells deposited or attached to the mineral particles is a composition comprising from 10 mg to 30 mg Hyaluronic acid per 1 mL of solution (comprising a buffer). In another embodiment, Hyaluronic acid composition for suspending cells deposited or attached to the mineral particles is a composition comprising from 10 mg to 25 mg Hyaluronic acid per 1 mL of solution (comprising a buffer). In another embodiment, Hyaluronic acid composition for suspending cells deposited or attached to the mineral particles is a composition comprising from 0.05% to 5% by weight Hyaluronic acid. In another embodiment, Hyaluronic acid composition for suspending cells deposited or attached to the mineral particles is a composition comprising from 0.1% to 1% by weight Hyaluronic acid. In another embodiment, Hyaluronic acid composition for suspending cells deposited or attached to the mineral particles is a composition comprising from 0.1% to 0.5% by weight Hyaluronic acid.

In another embodiment, Hyaluronic acid composition for suspending cells deposited or attached to the mineral particles is a solution. In another embodiment, Hyaluronic acid composition for suspending cells deposited or attached to the mineral particles is a gel.

The Carrier

In another embodiment, provided herein a bone-repair composition comprising a mineral particle. In another embodiment, mineral particles are in the form of a pulverized composition. In another embodiment, mineral particles are in the form of a micro-pulverized composition. In another embodiment, mineral particles comprise edges and grooves which provide more cell attachment sites.

In another embodiment, a mineral particle is a bone fiber. In another embodiment, a bone fiber of the invention has enhanced cell-binding surface. In another embodiment, a bone fiber of the invention is derived from a bone tissue. In another embodiment, a bone tissue is cut along its length or along the grain direction of the bone tissue to form a bone fiber.

In another embodiment, a mineral particle is a bone scaffold carrying a 3D cell culture. In another embodiment, a mineral particle is a bone mineral particle. In another embodiment, a mineral particle consists minerals. In another embodiment, a mineral particle comprises calcium phosphate. In another embodiment, a mineral particle comprises a calcium phosphate derivative. In another embodiment, a mineral particle comprises calcium sulfate. In another embodiment, a mineral particle comprises a calcium sulfate derivative. In another embodiment, a mineral particle comprises calcium hydroxyapatite. In another embodiment, a mineral particle comprises a silicate. In another embodiment, a mineral particle comprises a calcium sulfate derivative. In another embodiment, a mineral particle comprises a silicate mineral hydroxyapatite. In another embodiment, a mineral particle comprises beta-3 calcium phosphate. In another embodiment, a mineral particle comprises any combination of minerals known to one of skill in the art.

In another embodiment, a mineral particle has a diameter of at least 50 microns. In another embodiment, a mineral particle has a diameter of at least 100 microns. In another embodiment, a mineral particle has a diameter in the range of 50 microns to 2000 microns. In another embodiment, a mineral particle has a diameter in the range of 100 microns to 1000 microns. In another embodiment, a mineral particle has a diameter in the range of 200 microns to 2000 microns.

In another embodiment, a composition comprising particles and cells is grown and/or maintained with cell culture media for a period of at least a day. In another embodiment, a composition comprising particles and cells is grown and/or maintained with cell culture media for a period of at least two days. In another embodiment, a composition comprising particles and cells is grown and/or maintained with cell culture media for a period of 2 to 21 days. In another embodiment, a composition comprising particles and cells is grown and/or maintained with cell culture media for a period of 5 to 21 days. In another embodiment, a composition comprising particles and cells is grown and/or maintained with cell culture media for a period of 6 to 16 days. In another embodiment, a composition comprising particles and cells is grown and/or maintained with cell culture media for a period of 2 to 16 days. In another embodiment, a composition comprising particles and cells is grown and/or maintained with cell culture media for a period of 8 to 14 days.

Kit

In another embodiment, provided herein a kit comprising: a syringe, a mineral particle comprising endothelial cells and mesenchymal cells and/or osteoprogenitor cells organized in 2 or more cell layers attached thereto, and hyaluronic acid. In another embodiment, provided herein a kit comprising: a syringe, a mineral particle comprising Adipose Tissue derived Cells organized in 2 or more cell layers attached thereto, and hyaluronic acid. In another embodiment, provided herein a kit comprising: a syringe, a mineral particle comprising a 3D cell culture attached thereto, and hyaluronic acid. In another embodiment, provided herein a kit comprising: a syringe, a suspension comprising: mineral particles comprising a 3D cell culture attached thereto suspended in cell culture media, and hyaluronic acid. In another embodiment, a kit as described herein further comprises a composition comprising an anti-inflammatory agent.

In another embodiment, the pharmaceutical composition for filing a gap within a bone is produced by simply mixing hyaluronic acid and mineral particles comprising a 3D cell culture attached thereto. In another embodiment, the pharmaceutical composition for filing a gap within a bone is produced by simply mixing hyaluronic acid and a suspension comprising: mineral particles comprising a 3D cell culture attached thereto suspended in cell culture media.

In another embodiment, a kit for filing a gap within a bone, comprises a first part that contains an effective amount of hyaluronic acid, and a second part that contains an effective amount of a suspension comprising: mineral particles comprising a 3D cell culture attached thereto suspended in cell culture media. In another embodiment, the kit is for injection, and the first and second parts can be in solution form and are separately placed in independent packs (such as plastic bottles or glass bottles like ampoules). In another embodiment, each pack can comprise multiple dosages, but preferably a single dosage, of the first or second part. In another embodiment, prior to injection, the two parts are put into the injection syringe according to the information in the instruction (comprising the information such as the operation method of the kit, the mixing ratio of the solutions, etc.) to apply the formulation. In another embodiment, prior to injection, the two parts are put into a mixing means inside or outside the syringe. In another embodiment, prior to injection, the two parts are mixed by a mixing means inside or outside the syringe.

The proposed product contains 20-60% v/v Adipose Tissue derived Cells seeded on bone mineral particles for about 3-14 days.

The proposed product is based on a previous study which was based on the same materials; the difference is that the cells were not cultivated on the scaffold prior transplantation. The next section will detail results obtained in this study.

Treatment

In another embodiment, provided herein a method for filling a gap in a bone of a subject in need thereof, comprising the step of contacting the gap with a composition comprising: (a) a mineral particle, (b) endothelial cells and mesenchymal cells, and/or osteoprogenitor cells, and (3) hyaluronic acid, thereby filling a gap in a bone of a subject in need thereof. In another embodiment, provided herein a method for filling a gap in a bone of a subject in need thereof, comprising the step of contacting the gap with a composition comprising: a suspension comprising: mineral particles comprising a 3D cell culture attached thereto suspended in cell culture media and mixed in hyaluronic acid. In another embodiment, provided herein a method for filling a gap in a bone of a subject in need thereof, comprising the step of contacting the gap with a composition comprising: a suspension comprising: mineral particles comprising a 3D cell culture attached thereto suspended in hyaluronic acid. In another embodiment, contacting the gap is filling the gap with a composition as described herein. In another embodiment, contacting the gap is injecting a composition as described herein into the gap. In another embodiment, after contacting the gap and/or injecting a composition as described herein into the gap, the gap is further sealed. In another embodiment, composition for sealing a gap in a bone are known to one of average skill in the art.

In another embodiment, a composition of the invention suspended in hyaluronic acid is prepared for application directly on location. In another embodiment, a composition of the invention suspended in hyaluronic acid is injected under radiological control (such as but not limited to x-ray control). In another embodiment, a composition of the invention suspended in hyaluronic acid is injected into the center of the bone shaft.

In another embodiment, a gap in a bone is the result of a fracture. In another embodiment, the method of the invention is concerned with expediting bone repair and/or de-novo bone formation within a gap. In another embodiment, the method of the invention is concerned with repairing the periosteum. In another embodiment, the method of the invention is concerned with a vascular damage in proximity to the gap. In another embodiment, the method of the invention is concerned with inhibiting necrosis in the site of bone fracture or gap and inducing bone and vascular repair. In another embodiment, the method of the invention provides for bridging the fracture gap. In another embodiment, the method of the invention is directed to reinforcing and/or adding bone material to a trabecular zone.

In another embodiment, the method of the invention further provides minimizing motion by internal or external fixation. In another embodiment, the method of the invention further provides rigid fixation where there is absolutely no motion at the fracture site. In another embodiment, the method of the invention further provides bone gap healing under rigid fixation. In another embodiment, the method of the invention includes filling of the fracture gap with a composition as described herein.

In another embodiment, the method of the invention further provides repairing a fracture within a bone. In another embodiment, the method of the invention further provides repairing a gap within a bone. In another embodiment, the method of the invention further provides repairing a gap within a fractured bone. In another embodiment, the term "gap" is interchangeable with lesion. In another embodiment, a gap is at least 0.05 mm wide. In another embodiment, a gap is from 0.05 to 5 mm wide. In another embodiment, a gap is from 0.1 to 1 mm wide. In another embodiment, a gap is at least 0.05 mm deep. In another embodiment, a gap is from 0.05 to 20 mm deep. In another embodiment, a gap is from 0.1 to 15 mm deep. In another embodiment, a gap is from 0.5 to 10 mm deep. In another embodiment, a gap is from 0.5 to 5 mm deep.

In another embodiment, a gap is from 5 mm to 10 cm wide. In another embodiment, a gap is from 5 mm to 0.1 cm wide. In another embodiment, a gap is from 50 mm to 10 cm wide. In another embodiment, a gap is from 1 to 10 cm wide. In another embodiment, a gap is from 5 to 10 cm wide. In another embodiment, a gap is from 10 to 80 mm deep. In another embodiment, a gap is from 1 to 50 mm deep. In another embodiment, a gap is from 50 mm to 1 cm deep.

In another embodiment, the present invention provides a method that enhances, induces, and/or increases bone repair and restoration in a fractured bone as described herein. In another embodiment, the present invention restores bone density at a site formerly characterized by a gap. In another embodiment, the present invention restores the joint surface at the gap site.

In another embodiment, the present invention provides a method that is used for all kinds of bone fracture, bone-necrosis disease or bone repair. In another embodiment, the present invention provides a method wherein the bone-repair composition is directly injected into the region of bone loss/gap.

In another embodiment, the compositions of the invention comprise liquid solutions, emulsions, suspensions, gels and the like. In some embodiments, pharmaceutically-acceptable carriers suitable for preparation of such compositions are well known in the art. In some embodiments, liquid formulations include solutions, suspensions, dispersions, emulsions, oils and the like. In one embodiment, injectable compositions, of the invention are formulated in aqueous solutions, gels or suspensions. In one embodiment, injectable compositions of the invention are formulated in physiologically compatible buffers such as Hank's solution, Ringer's solution, or physiological salt buffer.

In some embodiments, formulations for injection are presented in unit dosage form, e.g., in ampoules or in multidose containers with optionally, an added preservative.

In one embodiment, compositions of the present invention are presented in a pack or dispenser device, such as an FDA approved kit, which contain one or more unit dosage forms containing the active composition. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Process of Making the Bone Repair Composition

The present invention also provides, in at least some embodiments, a method of producing the prosthetic implant described above, the method comprising the steps of isolation, expansion and co-cultivation of at least two types of cells onto mineral particles.

In another embodiment, each type of cells is first cultivated and expanded separately. Next the various types of cells are cultivated and co-expanded ex vivo under sterile conditions on the mineral particles, using conventional culture medium, such as DMEM, RPMI, with supplements of human serum (from autologous or allogeneic sources) or animal serum, or in serum-free media that allows the attachment and growth of adherent cells. In some embodiments, culture medium that supported the initial growth and expansion phase of these cells may optionally be replaced by another cell culture formula that supports the differentiation of these cells and bone formation.

In another embodiment, cells are expanded and co-cultivated in a dedicated bioreactor system. In another embodiment, a dynamic flow system, such as a bioreactor for example, stimulates optimal cell density and cell viability of a 3D cell culture.

In another embodiment, the bioreactor is described in detail in U.S. Pat. No. 6,911,201, which is incorporated by reference as if fully set forth herein. In this patent, a plug flow bioreactor system which allows the growth and prolonged maintenance of high density cell cultures that closely mimics the bone marrow microenvironment. In another embodiment, the bioreactor comprises a medium reservoir; gas mixture container; gas filters; injection points; plugs or containers of various sized plugs containing the mineral particles; flow monitors; flow valves; conditioned medium collecting and separating container; container for medium exchange; peristaltic pump; sampling point; container for medium exchange; monitor; steering device; and a pH probe. In another embodiment, a bioreactor that can be used according to the invention is described in United States Patent Publication No. US20120003185 which is hereby incorporated by reference in its entirety. In another embodiment, a dynamic flow bioreactor ensures the growth, longevity and differentiation of cell within the 3D cell culture.

In another embodiment, a 3D heterogeneous cell culture grown on a mineral particle is obtained by subjecting the cells attached to the mineral particles to flow-through bioreactor system. In another embodiment, the growth medium (cell media) is supplemented with growth factors and cytokines, such as, for example, one or more of: transforming growth factor beta (TGF beta), insulin-like growth factor-1 (IGF-1), osteogenic protein-1 (OP-1), fibroblast growth factor (FGF) members like FGF-2, FGF-9 and FGF-10 and members of bone morphogenic proteins (BMP) especially BMP-2, BMP-4 and BMP-7.

In another embodiment, a mineral particle covered by a 3D heterogeneous cell culture is transplanted into a predetermined site of bone loss or gap.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Example 1

In Vivo Studies Using First Generation Adipose Tissue Derived Cells Based Product Intra Femoral Injection Rat Model Adipose Tissue derived Cells were evaluated for their ability to form new bone after femoral injection into the femur shaft. An injectable formulation containing the following components was prepared; the ingredients were 20% PBS containing Adipose Tissue derived Cells and 1 ug/ml rhBMP-2 (R&D Systems, US), 20 mg OraGraft mineral particles (freeze-dried bone allograft obtained from human bone, LifeNet Health, Inc. Va., USA), 60% hyaluronic acid (Bio-Technology General LTD, Israel). Sprague-Dawley rats were anaesthetized. Under aseptic conditions, a longitudinal incision was made over the knee. Skin and muscles were held aside to expose the femoral condyle. Using a trephine bit drill a hole was drilled into the inter-condylar notch and through the trabecular area of the femur into the femoral shaft. Flushing of the rat's bone marrow with saline was done using an 18 gauge needle until no bone marrow was left. 150 microliters of the injection mixture was injected to fill the shaft. The hole in the condyle was blocked using bone wax and the muscles and skin were sutured. All animals recovered well from the surgery with no visible restrictions in their movements. Animals were weighed before and at the end of the experiment and no body weight loss was observed as a result of the surgery.

The experiment included two time points, 8 and 16 weeks. At first we evaluated the effect of 3 or $5 \times 10^6$ Adipose Tissue derived Cells per leg in comparison to non-treated leg and to vehicle group containing no cells (control). At 8 weeks, mechanical testing using the 4 point bending method was used. The results clearly demonstrated that femurs treated with Adipose derived cells endured more mechanical force until they broke as compared to untreated leg. The difference was not significant (FIG. 1).

Figure 2A:
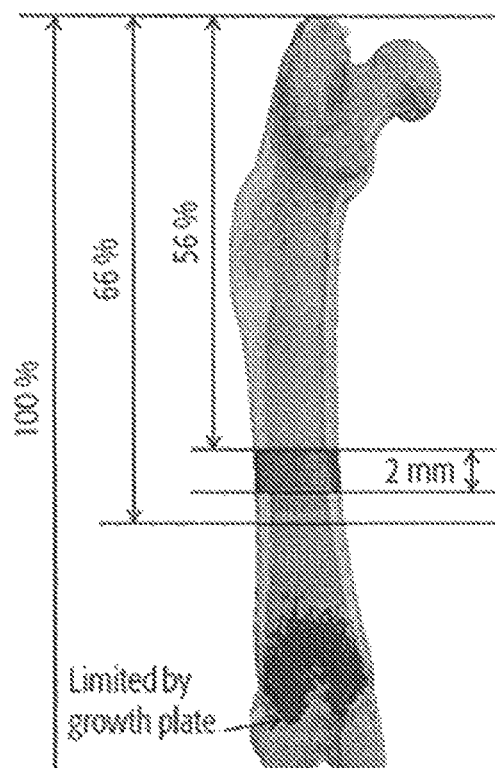
FIG. 2 is a scheme showing the automatic identification of the three compartments used for microCTanalysis. A) Femur is semi-transparent color with trabecular bone and cortical ring (yellow). B) Cortical mask is semi-transparent and bone within the mask is solid. C) Trabecular mask is semi-transparent and bone within the mask is solid.
Figure 2B:
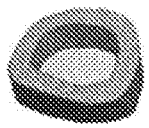
Figure 2C:
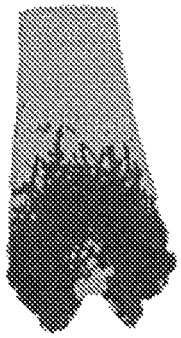

At 16 weeks (the end of the study), treated femurs were subjected to microCT scan and analysis. The analysis was done on three areas of the femur as illustrated in the image bellow: full bone, the metaphyseal trabecular bone and a cortical ring in the diaphysis (FIG. 2).

Scan and 3D images of treated legs clearly show bone fill-up with dense material. Bone fill-up was seen in legs treated with Scaffold (mineral particle) and 3 or 5 million cells and minimally seen in Scaffold only treated legs (FIG. 3).

MicroCT analysis revealed that on an organ level (full compartment), the bone volume density (AVD) of the Scaffold (mineral particle) and Adipose Tissue derived Cells (5 and 3 million cells) groups were higher than AVD value in the Scaffold only group.

Figure 4:
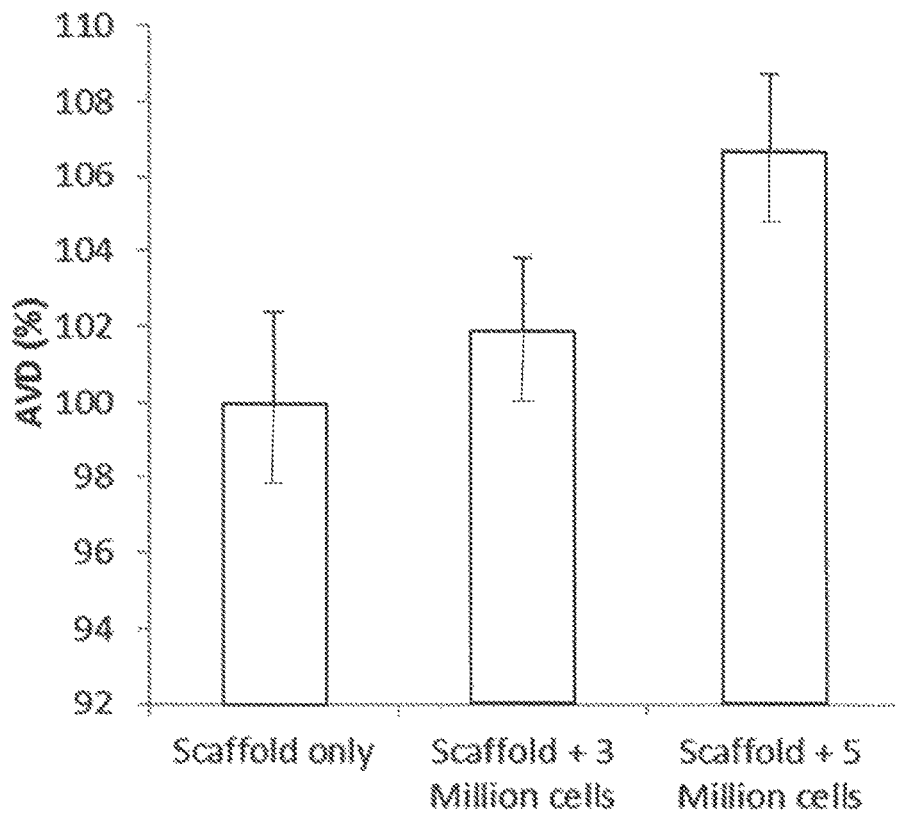
FIG. 4 is a bar graph showing full bone parameters—On an organ level (full compartment), the bone volume density (AVD) of group $5\times10^6$ cells appeared to be the highest and the values from group $3\times10^6$ appeared to be the lowest. Results are expressed as mean±SEM.
Figure 5A:
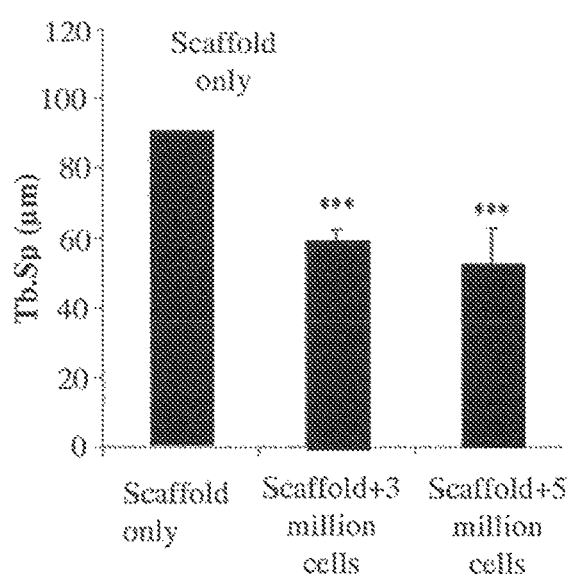
FIG. 5 are bar graphs showing the Trabecular bone parameters/measures—several microstructural bone parameters were measured, in all measurements the scaffold containing $5\times10^6$ cells group was superior to scaffold containing $3\times10^6$ group and to the scaffold only group. (A) Trabecular separation (B) Trabecular number (C) Trabecular connectivity (D) Bone surface/total volume (E) Bone volume/Total volume. Results are expressed as mean±SEM. * $p<0.05$,  $p<0.001$, * $p<0.0001$, the difference is compared to scaffold only group.
Figure 5B:
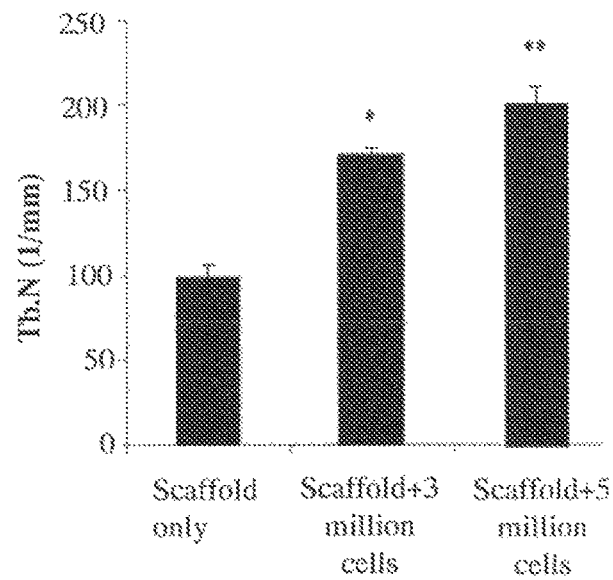
Figure 5C:
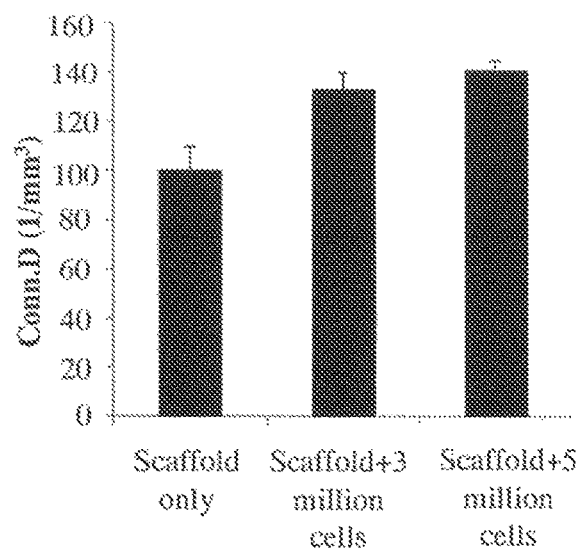
Figure 5D:
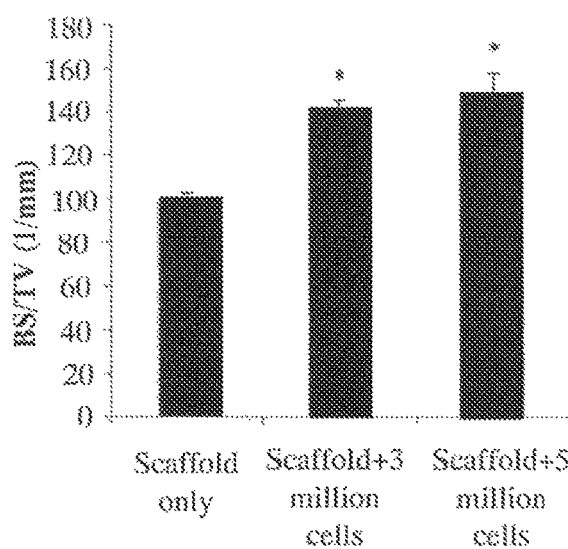
Figure 5E:
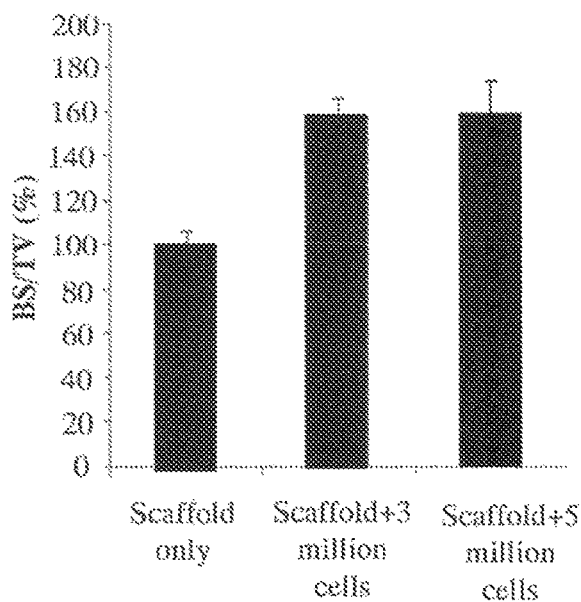

Furthermore, the AVD value in the 5 million Adipose Tissue derived Cells group was higher than the AVD value in the 3 million Adipose Tissue derived Cells group. However, the difference between the groups was not significant (FIG. 4).

On a micro-structural level it was found that in the trabecular region (TRAB) the scaffold only group had significantly lower BS/TV value, significantly higher trabecular separation (Tb.Sp) value and significantly lower trabecular number (Tb.N) value compared to the scaffold (mineral particle) and Adipose Tissue derived Cells (3 or 5 million) groups. Additionally, connectivity density (Conn.D) was lower in Scaffold only group compared to Scaffold (mineral particle) and 3 or 5 million Adipose Tissue derived Cells groups and BV/TV values were higher in scaffold (mineral particle) and Adipose Tissue derived Cells (3 or 5 million) groups compared to scaffold only group (FIG. 5).

In the cortex region, the cortical thickness (Ct.Th) values of scaffold (mineral particle) and Adipose Tissue derived Cells (5 and 3 million cells groups) were higher than the values of the scaffold (mineral particle) only group. The difference between the scaffold (mineral particle) and $5\times10^6$ group and the Scaffold only group was significant.

Figure 6A:
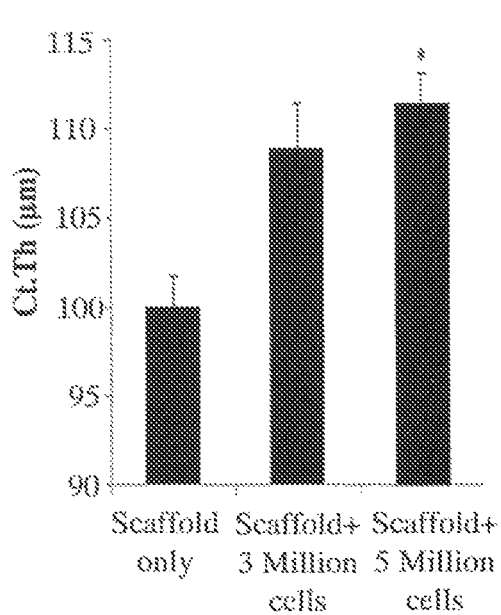
FIG. 6 are bar graphs showing Cortical bone parameters/measures—MicroCT scan results show that the scaffold containing $5\times10^6$ cells group was superior to scaffold containing $3\times10^6$ group and to the scaffold only group. (A) Cortical thickness (B) Bone volume. Results are expressed as mean±SEM. * $p<0.05$, the difference is compared to scaffold only group.
Figure 6B:
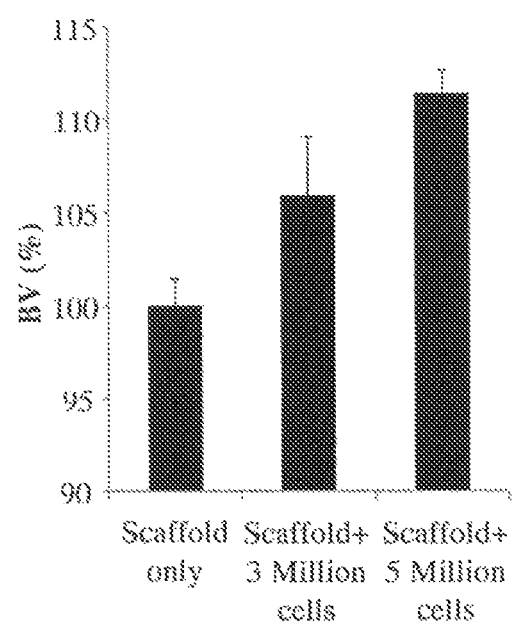

Bone volume (BV) values were higher in the scaffold (mineral particle) Adipose Tissue derived Cells (5 and 3 million cells) groups compared to scaffold only group (FIG. 6).

Figure 7A:
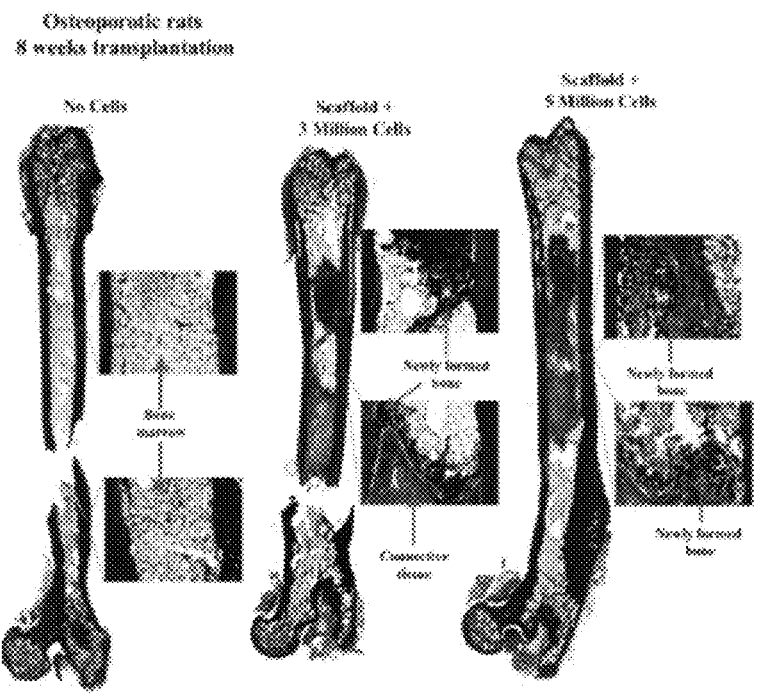
FIG. 7 is a micrograph and a bar graph showing Histology and morphometric analysis of both 8 and 16 weeks post transplantation groups. (A) 8 weeks post transplantation. (B) 16 weeks post transplantation. (C) Morphometric analysis of 3 slides from each femur in each group. Results are expressed as mean±SEM. #, * $p<0.05$, the difference is compared to scaffold only group.
Figure 7B:
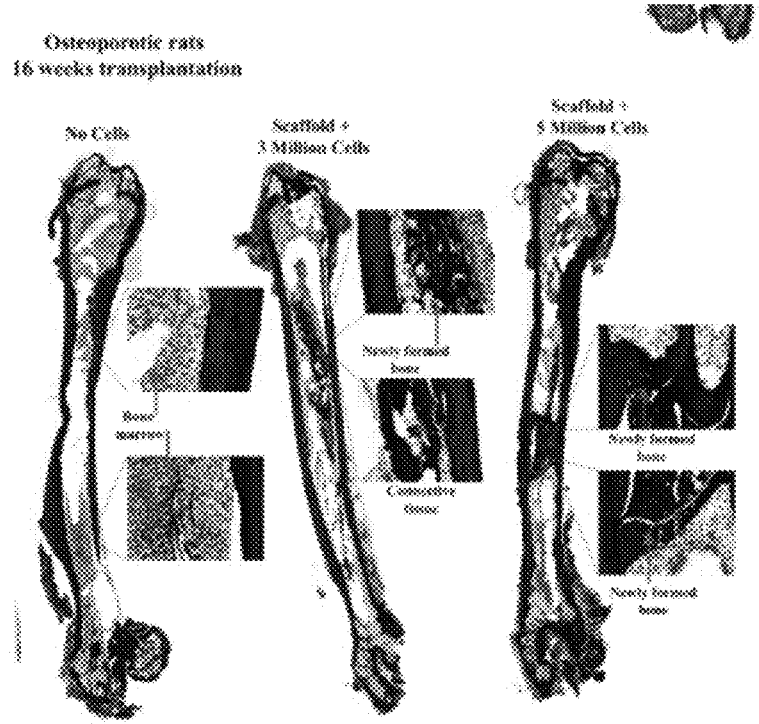
Figure 7C:
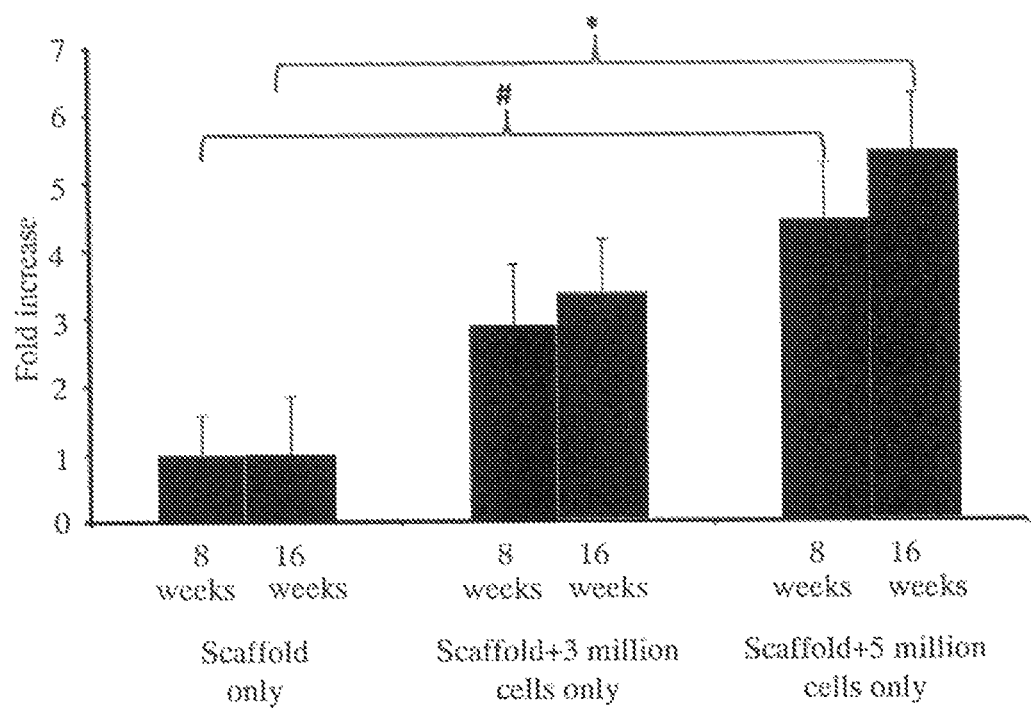

Femurs used for microCT and mechanical bending tests were taken to histological processing and analysis. Femurs sections were stained with picro serious red stain to highlight new formed bone (FIG. 7A, B). The histological sections were subjected to histomorphometry and measurements are shown and summarized in FIG. 7, Histomorphometry data reveals that the amount of new formed bone is with concordance to cell number and to the time from transplantation. Scaffold (30 mg of mineral particle) and $5\times10^6$ cells group surpassed Scaffold (30 mg of mineral particle) and $3\times10^6$ cells group and significantly surpassed the Scaffold only group in terms of the amount of new bone formed. Moreover, it can be seen that after 16 weeks the amount of grown bone was higher than of the other two groups.

Second Generation Adipose Tissue Derived Cells Based Product

As previously detailed the proposed product is based on bone mineral particles seeded with multicell Adipose Tissue derived Cells and suspended in hyaluronic acid.

Cell Attachment and Cultivation on Bone Mineral Particles $2.5\times10^5$ Cells were suspended in 100 µl medium and carefully added to 30 mg of bone mineral particles, in ventilated tubes (TRP, Innovation in plastic, Switzerland). The tubes were incubated for 1 h, in 37° C. to allow cell adhesion to the construct. Additional culture medium (2.9 mL) was then added to the tube. Following predetermined time points a quantitative analysis of cell attachment was conducted by nucleus cell counting. Cells were further stained with Gimsa in order to evaluate cell morphology and seeding homogeneity.

Figure 8A:
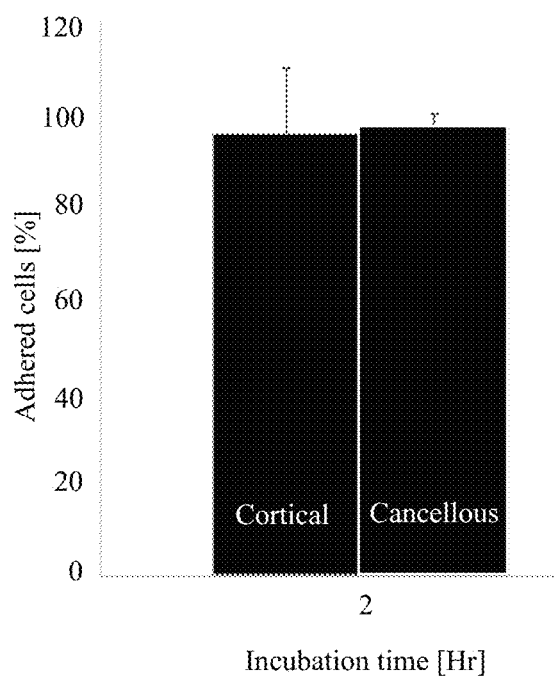
FIG. 8 is a bar graph and a micrograph showing seeded cells adhesion to scaffold. (A) Adipose tissue derived cells were seeded for 2 hours and cell numbers were quantified. (B) Gimsa Cell staining of seeded cells.
Figure 8B:

Results show that above 90% of the Adipose Tissue derived Cells attached to two different types of scaffolds after only 2 hours. Further incubation did not improve cell attachment. Gimsa stain showed that the cells spread and were homogenously distributed (FIG. 8).

Figure 9A:
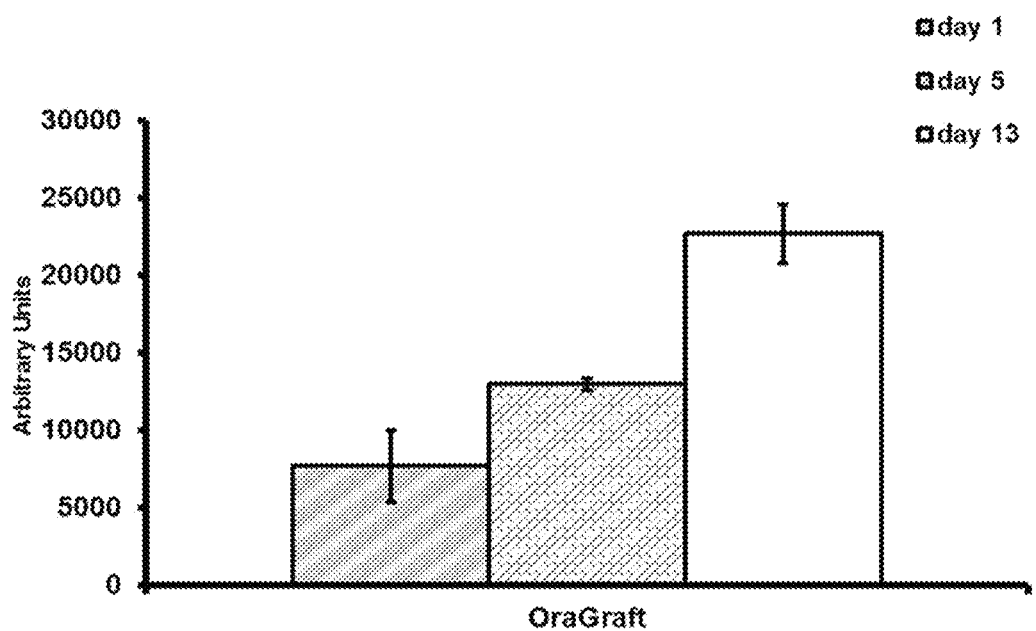
FIG. 9 is a bar graph and 2 micrographs showing (A) Cultivated Adipose tissue derived cells propagate for up to 13 days. (B, C) Cells generate multi cellular layers onto mineral particles. Histological and scanning electron microscope analysis shows the formation of multicellular layers on top of the bone mineral particles. These layers generate a typical connective tissue structure containing collagen fibers and polysaccharides as seen in Picro Sirius Red stain and Toluidine Blue stain, respectively.
Figure 9B:
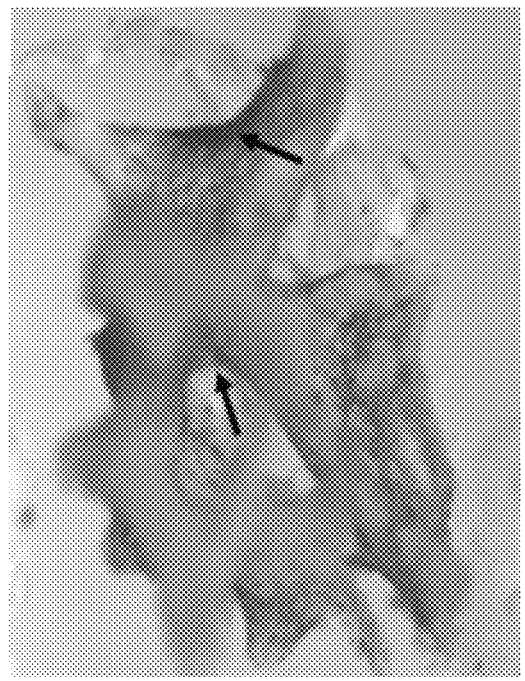
Figure 9C:
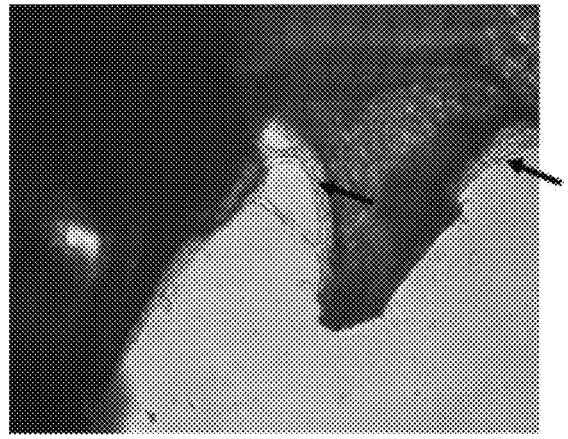

Further cultivation in 50 ml ventilated tubes showed that cells maintain their viability and proliferate. Furthermore, cells generated multi cellular layers onto the mineral particles (FIG. 9).

Histological and scanning electron microscope analysis shows the formation of multicellular layers on top of the bone mineral particles. These layers generate a typical connective tissue structure containing collagen fibers and polysaccharides as seen in Picro Sirius Red stain and Toluidine Blue stain, respectively (FIG. 10).

Figure 11:
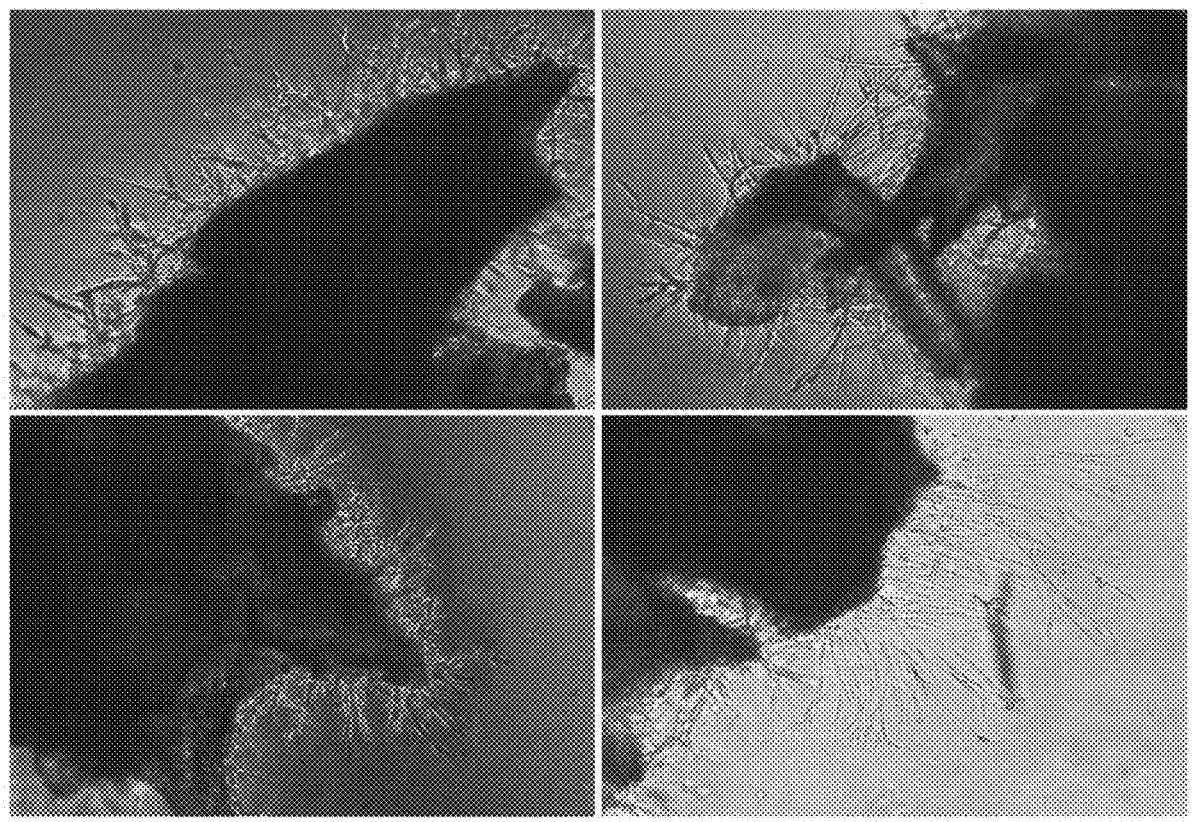
FIG. 11. Are micrographs showing the cells from the 3-D multi cell culture sprouting onto Matrigel after 72 hours culturing.

Both Adipose derived endothelial cells and mesenchymal stem cells were seeded as a co-culture on the scaffold. For evaluation of endothelial cell functionality, seeded particles were placed in Matrigel for predetermined time points. Adipose Tissue derived endothelial cells were shown to be able to attach to the Matrigel and to form sprouts out of the scaffold and out to the surrounding (FIG. 11).

What is claimed is:

1. A composition comprising (a) a mineral particle having a diameter in the range of 50 microns to 2,000 microns and endothelial cells and mesenchymal cells organized in 2 or more cell layers, wherein said 2 or more cell layers are attached to said mineral particle, wherein at least $1\times10^3$ endothelial and mesenchymal cells occupy 1 mg of said mineral particle, and (b) an injectable medium comprising hyaluronic acid and liquid solution, wherein said hyaluronic acid is present in an amount of 0.05% to 5% by weight of said injectable medium, said liquid solution comprises a physiological salt buffer, wherein said (a) is dispersed in said (b).

2. The composition of claim 1, further comprising a biocompatible binder.

3. The composition of claim 2, wherein said biocompatible binder is albumin.

4. The composition of claim 1, wherein said endothelial cells and said mesenchymal cells attached to said mineral particle comprise extracellular matrix nanoscale fibers.

5. The composition of claim 1, comprising adipose tissue derived cells.

6. The composition of claim 5, comprising 20% to 60% v/v said endothelial cells and mesenchymal cells, said adipose tissue derived cells, or both.

7. The composition of claim 1, wherein said mineral particle is bone mineral particle.

8. The composition of claim 1, wherein said mesenchymal cells comprise mesenchymal stem cells.

9. The composition of claim 1, wherein said mineral particle comprises: a calcium phosphate derivative, a calcium sulfate derivative, calcium hydroxyapatite, a silicate mineral hydroxyapatite, beta-3 calcium phosphate, or any combination thereof.

10. The composition of claim 1, wherein said particle has a diameter in the range of 100 microns to 1,000 microns.

11. The composition of claim 1, maintained in-vitro for 2 to 16 days.

12. A kit comprising: a syringe and the composition of claim 1.

13. The kit of claim 12, further comprising a mixing means.

14. A method for filling a gap in a bone of a subject in need thereof, comprising the step of contacting said gap with the composition of claim 1, thereby filling a gap in a bone of a subject in need thereof.

15. The composition of claim 1, wherein said hyaluronic acid has a molecular weight of 200,000 to 850,000 daltons.

* * * * *